US006855332B2

(12) United States Patent
Gizurarson et al.

(10) Patent No.: US 6,855,332 B2
(45) Date of Patent: Feb. 15, 2005

(54) ABSORPTION PROMOTING AGENT

(75) Inventors: Sveinbjorn Gizurarson, Reykjavik (IS); Sigridur Olafsdottir, Reykjavik (IS); Jakob Lindal Kristinsson, Reykjavik (IS); Kolbrun Hrafnkelsdottir, Reykjavik (IS); David Rurik Olafsson, Reykjavik (IS); Oddur Ingolfsson, Reykjavik (IS); Ellen Ruth Ingimundardottir, Mosfellsbaer (IS)

(73) Assignee: Lyfjathroun hf., Reykjavik (IS)

( * ) Notice: Subject to any disclaimer, the term of this patent is extended or adjusted under 35 U.S.C. 154(b) by 0 days.

(21) Appl. No.: 10/208,658

(22) Filed: Jul. 29, 2002

(65) Prior Publication Data

US 2004/0005275 A1 Jan. 8, 2004

(30) Foreign Application Priority Data

Jul. 3, 2002 (IS) .................................................... 6453

(51) Int. Cl.[7] .............................. A61K 9/00; A61K 9/66; A61F 13/00
(52) U.S. Cl. ..................... 424/434; 424/455; 424/450; 514/547; 514/941; 514/946
(58) Field of Search ................................. 424/434, 455, 424/450, 45, 46; 514/547, 941, 946, 3

(56) References Cited

U.S. PATENT DOCUMENTS

| 4,349,540 | A | 9/1982 | D'Hinterland et al. |
| 4,567,161 | A | 1/1986 | Posanski et al. |
| 5,019,395 | A | 5/1991 | Mahjour et al. |
| 5,177,091 | A | 1/1993 | Feige et al. |
| 5,190,748 | A | 3/1993 | Bachynsky et al. |
| 5,314,685 | A | 5/1994 | Tyle et al. |
| 5,645,856 | A | 7/1997 | Lacy et al. |
| 5,646,109 | A | 7/1997 | Owen et al. |
| 5,719,122 | A | 2/1998 | Chiodini et al. |
| 5,942,237 | A | 8/1999 | Gizurarson et al. |
| 6,008,228 | A | 12/1999 | Bailey et al. |
| 6,013,277 | A | 1/2000 | Curri |
| 6,096,338 | A | 8/2000 | Lacy et al. |
| 6,190,695 | B1 | 2/2001 | Hoshino et al. |
| 6,217,902 | B1 | 4/2001 | Tanner et al. |
| 6,267,985 | B1 | 7/2001 | Chen et al. |
| 6,294,192 | B1 | 9/2001 | Patel et al. |
| 6,309,663 | B1 * | 10/2001 | Patel et al. ............ 424/450 |
| 6,326,401 | B1 | 12/2001 | Chauveau et al. |
| 6,383,471 | B1 | 5/2002 | Chen et al. |
| 6,384,034 | B2 | 5/2002 | Simitchieva et al. |
| 6,410,046 | B1 | 6/2002 | Lerner |
| 6,451,339 | B2 | 9/2002 | Patel et al. |
| 6,458,383 | B2 | 10/2002 | Chen et al. |
| 6,468,559 | B1 | 10/2002 | Chen et al. |
| 6,476,042 | B1 | 11/2002 | Harrison |
| 6,495,596 | B1 | 12/2002 | Keller |
| 6,514,503 | B1 | 2/2003 | Gizurarson et al. |
| 2001/0024658 | A1 | 9/2001 | Chen et al. |
| 2002/0012673 | A1 | 1/2002 | Schroder |
| 2002/0025509 | A1 * | 2/2002 | Cima et al. ............. 435/4 |
| 2002/0032171 | A1 | 3/2002 | Chen et al. |
| 2003/0077297 | A1 | 4/2003 | Chen et al. |
| 2003/0104048 | A1 | 6/2003 | Patel et al. |
| 2003/0219472 | A1 | 11/2003 | Pauletti et al. |
| 2003/0220391 | A1 | 11/2003 | Borgardus et al. |
| 2003/0232078 | A1 | 12/2003 | Dong et al. |
| 2003/0235595 | A1 | 12/2003 | Chen et al. |
| 2003/0236236 | A1 | 12/2003 | Chen et al. |

FOREIGN PATENT DOCUMENTS

| EP | 0 544 612 A2 | 6/1993 |
| EP | 0351651 B1 | 9/1993 |
| WO | WO 99/02186 | 1/1999 |
| WO | WO 03/016350 A1 | 2/2003 |

OTHER PUBLICATIONS

GlaxoSmithKline, Imitrex® (sumatriptan succinate), Drug Facts and Comparisons, p. 855, 2000.*
Lippold, B.C. and Ohm, A.M., "Effects of Surfactants, Polymers and Gastric Juice on Contact Angle of Drugs," Acta Pharm. Technol., 32(1):20–25 (1986).
Zakrzewski, Z., et al., "The Effects of Adjuvants on the Physical Properties and Active–Substance Release from Oral Suspensions," Goldschmidt Informiert, 57:14–17 (1982).

* cited by examiner

Primary Examiner—Gary Kunz
Assistant Examiner—Mina Haghighatian
(74) Attorney, Agent, or Firm—Hamilton, Brook, Smith & Reynolds, P.C.

(57) ABSTRACT

The present invention relates to pharmaceutical compositions comprising polyoxyethylene glycol, fatty acid mono- and diglyceride ester as an absorption promoting agent and an absorption controlling agent together with a therapeutically, prophylactically and/or diagnostically active substance. The pharmaceutical compositions are especially suitable for mucosal administration such as intranasal administration.

32 Claims, 1 Drawing Sheet

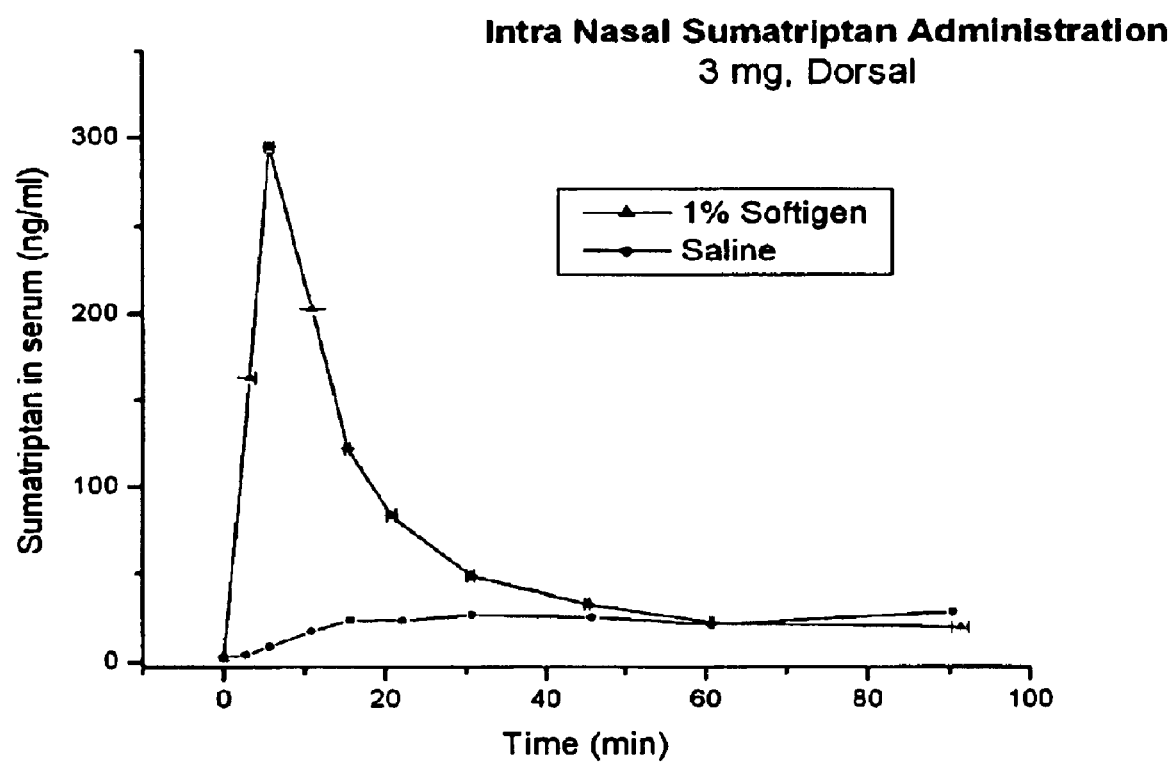
FIGURE

ABSORPTION PROMOTING AGENT

RELATED APPLICATION

This application claims priority under 35 U.S.C. § 119 or 365 to Icelandic Application No. 6453 filed Jul. 3, 2002. The entire teachings of the above application are incorporated herein by reference.

BACKGROUND OF THE INVENTION

Parenteral administration (intravenous, intramuscular and subcutaneous) of biologically active agents, such as drugs, is normally regarded as the most effective route of administration. However, administration by injection has a number of disadvantages. Injection of a biologically active agent requires the use of sterile syringes and administration by trained personnel, and may cause pain and irritation, particularly in the case of repeated injections. This route of administration poses a risk of infection. More significantly, intramuscular injections are often poorly tolerated by the individual, and may possibly cause an induration (hardening of tissue), haemorrhage (bleeding) and/or necrosis (local death of tissue) at the injection site.

The mucosal membrane is connected to an extensive network of blood capillaries under the nasal mucosa, which makes the membrane highly suitable for drug delivery (delivery of biologically active agents), particularly suited to provide rapid absorption of biologically active agents, providing a rapid pharmacological response. One example of such a mucosal membrane is the nasal epithelial membrane, which consists essentially of a single layer of epithelial cells (pseudostratified epithelium), the mucosal membrane is therefore very suitable for drug delivery.

A variety of vehicle systems for intranasal drug delivery have been developed. One of the problems encountered in using such vehicle systems, is the local irritation and lack of rapid absorption. Without the rapid rate of absorption, the biologically active agents, such as drug substances, may be cleared from the absorption site before they are absorbed into the systemic circulation, into the lymphatic system or into the brain, whichever is relevant.

SUMMARY OF THE INVENTION

The present invention provides pharmaceutical compositions, which when administered to the mucosa such as intranasally to the nasal mucosa enable the active substance rapidly to be absorbed into the circulatory system. The compositions comprise an absorption promoting and/or controlling agent that is a glyceride ester formed by esterification of glycerol with one or more polyethylene glycols and with one or more fatty acids. The absorption promoting and/or controlling agent does not irritate the nasal mucosa in the concentrations claimed.

Accordingly, the present invention relates to a pharmaceutical composition for nasal administration, comprising:

i) a PEG-fatty acid-mono- or diglyceride having the formula (I):

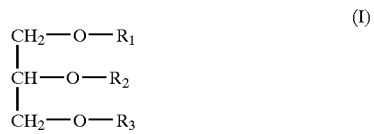

(I)

wherein R1, R2, and R3 are independently selected from the group consisting of C6 to C22 fatty acids, PEG polymers and hydrogen, provided that it contains at least one C6–C22 fatty acid and at least one PEG polymer;

ii) a therapeutically, prophylactically and/or diagnostically active substance; and iii) optionally, a physiologically acceptable vehicle.

Component i) is considered as an absorption promoting or controlling substance.

The term "PEG-C6/C22 glycerides" as used in the present context refers to those reaction products derived from the co-reaction of polyoxyethylene glycol (or polymerizable precursor thereof, such as ethylene oxide) with a C6–C22 carboxylic acid and glycerol or a C6–C22 carboxylic acid glyceride or glycerides. Resulting from such reactions are, typically, mixtures of a polyoxyethylene glycol-C8–C10 carboxylic acid di/tri-glyceride esters (e.g., PEG-glycerol-caprate, PEG-glycerol-caprylate etc.) as principal components.

In another aspect, the invention relates to a pharmaceutical composition, comprising:

i) from about 0.005% to about 2.5% v/v of a PEG-fatty acid-mono- or diglyceride having the formula (I):

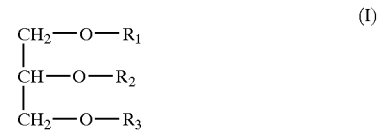

(I)

wherein R1, R2, and R3 are independently selected from the group consisting of from C6 to C22 fatty acids, PEG polymers and hydrogen, provided that it contains at least one C6–C22 fatty acid and at least one PEG polymer;

ii) a therapeutically, prophylactically and/or diagnostically active substance; and iii) optionally, a physiologically acceptable vehicle.

Other aspects of the invention relates to a method for obtaining a relatively fast onset of a therapeutic effect or for improving the bioavailability of an active substance, the method comprises administering to a mammal including a human an efficient amount of a composition according to the invention.

BRIEF DESCRIPTION OF THE DRAWING

The foregoing and other objects, features and advantages of the invention will be apparent from the following more particular description of preferred embodiments of the invention.

The FIGURE is a graph illustrating the rapid and efficient absorption of sumatriptan into serum using a composition of the invention relative to that of a corresponding saline solution.

DETAILED DESCRIPTION OF THE INVENTION

A description of preferred embodiments of the invention follows.

The present invention concerns pharmaceutical compositions especially suitable for administration to a mucosal membrane. The invention is based on the observation that specific glyceride esters can act as absorption promoters and at the same time they are non-irritating to the nasal mucosal membrane.

The absorption-promoting agent can be the product of an esterification reaction between a polyoxyethylene glycol, glycerol and one or more straight chain C6–C22 carboxylic acids. Alternatively the component may be prepared by oligomerizing or polymerising ethylene oxide in the presence of an ester of glycerol and one or more of such C6–C22 carboxylic acids (glyceride esters). Still another route, and the preferred one is by reacting a carboxylic acid glyceride ester or esters with a fully pre-formed polyoxyethylene glycerol under conditions to achieve alcoholysis. The term "carboxylic acid glyceride ester", is employed in this description in the conventional sense to mean an ester which has been derived from glycerol and a carboxylic acid.

Suitable absorption enhancing agents for use in this invention, which are commercially available, are Softigen™ 767, produced by Condea Chemie GmbH (Witten, Germany) and Labrasol™, produced by Gattefosse Corp. (Paris, France). Softigen™ 767 contains following specifications:

| Specification | Value |
| --- | --- |
| Acid value | ≦1 mg KOH/g |
| Saponification value | 90–100 mg KOH/g |
| Iodine value | ≦1 mg I/100 mg |
| Colour | ≦150 APHA |
| Freeze test | Clear solution at 0° C. (24h) |
| Water content | max. 0.5% (Carl Fisher test) |
| Viscosity | 150–175 mPa × s |
| Refractive index | 1.464–1.466 $^n$D20 |

EP-0351651 describes the use of PEG-C8/C10-glycerides as an absorption promoter for insulin. Especially for orally and buccally administered insulin. From the disclosure it appears that an increase in concentration of PEG-C8/C10-glycerides results in an increase in absorption. With respect to a nasal composition the composition described has a relatively high concentration of absorption enhancer, namely about 50% w/w.

The present invention provides a glyceride, which can be used as an absorption promoting agent and an absorption controlling agent in the concentrations claimed in the appended claims. It is especially interesting that the present inventors have observed that also very low concentrations lead to a suitable therapeutic response. Thus, even concentrations in a range corresponding to from about 0.005% to about 2.5%, or from about 0.01% to about 2.0% are suitable for the administration of biologically active substances, such as drugs, through the mucosal membrane such as the nasal membrane. This substance is fully water-soluble and produces a non-viscous solution together with water or saline. The substance of the present invention provides enhanced absorption of the biologically active agent through the nasal mucosal membrane. Use of the invention provides the ability to achieve a significant controllable systemic absorption of biologically active agents such as drugs, into the systemic circulation, without causing unacceptable irritation of the epithelial membrane.

As mentioned above, the disclosure in EP-B-0 351 651 (Hoffmann-La Roche) is focused on oral and buccal insulin composition. The present invention is mainly directed to nasal compositions, but as discussed above, it has been found that even very small concentrations of PEG-fatty acid-glycerides may lead to a suitable therapeutic response. The present invention is therefore also directed to compositions in general, in which the concentration of the absorption promoting or controlling agent is relatively low, namely in concentrations ranging from about 0.005% to about 2.5% v/v such as, from about 0.01% to about 2% v/v of chemically modified glycerides selected from the group consisting of monoglycerides, diglycerides, and mixtures thereof, said glycerides having the formula (I):

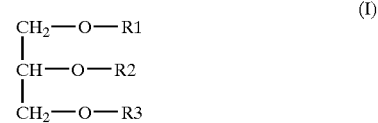

wherein R1, R2 and R3 are as defined above.

The fatty acid component is a C6–C18 fatty acid, saturated or unsaturated, such as C6–C14 fatty acid or a C8 or C10 fatty acid or combination thereof. Examples of C6 to C18 carboxylic acids, which are useful for the R1, R2 or R3 component in formula (I) above are caproic, caprylic, capric, lauric, myristic, oleic, palmitic and stearic acid. Especially suitable for this invention are capric and caprylic acids, individually or together.

The polyoxyethylene glycol (PEG or PEO) component used in the formation of the absorption promoter is, typically, a medium to high molecular weight material having a molecular weight of from about 200 to about 1200 such as, e.g., from about 300 to about 600.

Normally, the PEG polymer comprises PEG$_{2-30}$ residues of polyoxyethylene, having 2–30 polyoxyethylene units, such as, e.g., a PEG$_{2-20}$ residue of polyoxyethylene having from 2 to 20 polyethylene units, a PEG$_{3-10}$ residue of polyoxyethylene having 3 to 10 polyoxyethylene units or a PEG$_{3-6}$ residue of polyoxyethylene having 3 to 6 polyoxyethylene units.

In a composition according to the present invention for nasal administration the concentration of component i) in the composition is at the most 50% v/v such as, e.g., from about 0.005% to about 50% v/v, from about 0.005% to about 40% v/v, from about 0.01% to about 30% v/v, from about 0.01% to about 25% v/v, from about 0.01 to about 20% v/v, from about 0.01 to about 15% v/v, or from about 0.01 to about 10% v/v. Alternatively, the concentration of component i) in the composition is at the most about 10% v/v such as, e.g., at the most about 7.5% v/v, at the most about 5% v/v, or at the most 2.5% v/v.

Irrespective of the route of administration, the invention relates to a composition having a concentration of component i) in the composition in an amount of from about 0.01% to about 2% v/v such as, e.g., from about 0.1 to about 1.5% v/v, such as from about 0.2% to about 1% v/v.

As mentioned above, a composition according to the invention leads to a relatively fast onset of the active substance contained in the composition. Thus, $t_{max}$, when nasally administered, takes places relatively fast after administration compared to $t_{max}$ obtained after administration of a similar composition containing saline instead of component i). In other words, in a composition according to the invention, the PEG-fatty acid mono- or diglycerides are used as an absorption-promoting agent or an absorption controlling agent, providing a desired $t_{max}$.

A further advantage of a composition according to the invention is that an increase in bioavailability is obtained. Thus, when nasally administered, the bioavailability is increased with a factor of at least 2 such as, e.g., at least 5, at least 10, at least 20, at least 40 compared with the bioavailability obtained after administration of a similar composition containing saline instead of component i).

In a particular embodiment, a composition according to the invention contains the active substance ii) that is in a dissolved form.

A composition according to the invention may further comprise one or more components selected from the group consisting of: surfactants, water absorbing polymers, substances which inhibit enzymatic degradation, alcohols, organic solvents, oils, pH-controlling agents, solubilizers, stabilizers, HLB-controlling agents, viscosity controlling agents, preservatives, osmotic pressure controlling agents, propellants, air displacement, water, and mixtures thereof.

In a particular embodiment, the $PEG_{2-30}$ is polyoxyethylene, having 2–30 monomer units, and more preferably, $PEG_{3-6}$ having 3 to 6 polyoxyethylene units.

The composition of the invention promotes the absorption of biologically active agents, such as drugs, across the nasal membrane, that is, the drug is capable of being absorbed into the systemic circulation with sufficient speed and quantity to be biologically active. This can be accomplished, since an absorption promoter increases the rate of absorption allowing a rapid onset of the drug and increases the amount absorbed across the nasal membrane.

For intranasal administration, a biologically active agent must be applied to the mucosa in such a manner that it is able to penetrate or be absorbed through the mucosa into the systemic circulation before it is washed away by the nasal secretions or ciliary beat clearance. In order to penetrate the mucus, the delivery vehicle must have a certain degree of biocompatibility with the mucus membrane and hence have a certain degree of hydrophilicity and hydrophobicity. Work described herein relates to the utility of compositions described herein as absorption-promoting agents. Accordingly, this invention also pertains to compositions, e.g., biologically active agent such as drug compositions, comprising a biologically active agent and an absorption-promoting agent containing 0.01–2% v/v of glycerides selected from the group consisting of PEG-C8/C10-glycerides.

The PEG-C8/C10 glycerides are products derived from the co-reaction of polyoxyethylene glycol (or polymerizable precursor thereof, such as ethylene oxide) with a C6–C22 carboxylic acid and glycerol with a C6–C22 carboxylic acid glyceride or glycerides. Resulting from such reactions are, typically, mixtures of a polyoxyethylene glycol-C6–C22 carboxylic acid mono-/di-glyceride esters (e.g., PEG-C8/C10-glycerol-dicaprate, diPEG-glycerol-caprate, PEG-glycerol-dicaprylate etc.) as principal components. The product may also be produced by an esterification reaction between a polyoxyethylene glycol, glycerol and one or more straight chain C6–C22 carboxylic acids. Alternatively the component may be prepared by oligomerizing or polymerizing ethylene oxide in the presence of an ester of glycerol and one or more of such C6–C22 carboxylic acids (glyceride esters). Still another route, and the preferred one is by constant pressure-reacting a carboxylic acid glyceride ester or esters with a fully pre-formed polyoxyethylen glycerol under conditions to achieve alcoholysis. The term "carboxylic acid glyceride ester", is employed in these description in the conventional sense to mean an ester which has been derived from glycerol and a carboxylic acid.

The absorbtion promoting compositions of the invention modulate the absorption of a biologically active substance such as a drug in order to generate successful absorption and absorption rate into the systemic circulation.

In this invention, a biologically active agent is combined with PEG-fatty acid-glyceride according to this present invention, and this formulation can be used to elicit absorption of the drug in a vertebrate such as any mammalian host or more specifically a human. Examples of biologically active substances and drugs are anti-emetics and anti-nausea and drugs for the treatment of motion sickness such as ondansetron, granisetron, tropisetron, scopolamine, metopimazine; anti-migraine drugs such as sumatriptan, zolmitriptan, naratriptan, rizatriptan, eletriptan, almotriptan, frovatriptan; sex hormones, such as androgen hormones, e.g., testosteron and derivatives thereof; anti-narcotic treatment drugs such as nicotine, hormones such as calcitonin, drugs for the treatment of erectile dysfunction such as apomorphine, sildenafil, drugs for pain management such as morphine, drugs for sleep induction such as melatonin and the benzodiazepines, drugs for sedation, preanaestesia and treatment of epileptic seizures from the group of benzodiazepines such as diazepam, alprazolam, flunitrazepam, lorazepam, triazolam, nitrazepam, lormetazepam, midazolam, desmethyldiazepam, flurazepam; drugs for antithrombotic treatment such as heparin, dalteparin, enoxaparin and tranexamic acid; drugs for fertility treatment such as choriogonadotropin, menotropin, follitropin alpha, follitropin beta and lutropin alpha.

Other biologically active agents include but are not limited to materials having antiviral, antiprion, antibacterial, antineoplastic, antiparasitic, anti-inflammatory and/or antifungal activity. They may act as neurotransmitter, neuromodulators, hormone, hormone releasing factor, hormone receptor agonist or antagonist. The agent may also be an activator or inhibitor of a specific enzyme, an antioxidant, a free radical scavenger or a metal chelating agent. The agent may further be any substance which is capable of acting as a stimulant, sedative, hypnotic, analgesic, anticonvulsant, antiemetic, anxiolytic, antidepressant, tranquillizer, cognition enhancer, agents preventing or healing amnesia, metabolic stimulator or inhibitor, appetite stimulator or inhibitor and/or narcotic antagonist or agonist. The agent may furthermore be any bioactive material found to be deficient in conjunction with the disorder being treated or prevented, for example, nutrients such as glucose, ketone bodies, and the like, or metabolic precursors such as lecithin, choline or acetyl coenzyme A for producing neurotransmitters for the treatment of Alzheimer's disease or insulin for the treatment of obesity and diabetes. The agent may also be an antibody for the treatment of viral, bacterial, prion, parasitic infections or tumours and/or cancer or for diagnosis of diseases or disorders where polyclonal or monoclonal antibodies and/or/with biochemical markers characteristic of the diseases or disorder are used. Such diagnostic antibodies may be labelled with any labelling agent who may be suitable according to the invention. Gene manipulated microorganisms may also be used for the treatment of tumours and/or cancer. The biologically active substance may also comprise of substances selected from the group consisting of adrenal hormones, corticosterodis and derivatives, amino acids, anorectics, antibiotics, anti-allergic agents, antibodies, anticholinergic agents, anti-depressants, anti-epileptica and anti-spasmolytica, anti-histaminic agents, anti-hypertensive agents, anti-inflammatory agents (enzymatic or non-steroidal or steroidal), anti-neoplastic agents, antiseptics, anti-tumor, anti-tussive expectorant (asthmatic agents), anti-viral and anti-cancer agents, beta-adrenergic blocking agents, blood factors such as factor VII, factor VIII etc, metabolism controlling agents, bone-metabolism controlling agents, bronchodilators, cardiotonics, cardiovascular regulatory hormones, chemoterapeutic agents, CNS-stimulants, diagnostic drugs, dopaminergic agents, enzymes, gastrointestinal hormones, hypothalamus hormones and derivatives, hypotensives, local anesthetics, migraine treatment substances, narcotics, antagonists and analgetics, pancreatic hormones and derivatives, parasympathomimetics, parasympatholytics, Parkinson's disease substances, pituitary gland hormones and derivatives, prostaglandines, protease inhibitors, sedatives, sex-hormones, sympathomimetics, thyroid gland hormones and derivatives, tranquillisers, vasoconstrictors, vasodilators, and vitamins.

The biologically active agent such as drugs may be used in a particulate form or dissolved. The formulation is especially suitable for dissolved drugs.

The absorption promoting effect on an absorption promoters according to this invention can be monitored with methods known in the art, such as HPLC, LC-MS, LC-MS-MS, GC, GC-MS, spectroscopy and/or ELISA assays. As used herein, "absorption promoting effect and absorption enhancing effect" is intended to mean the ability to increase and/or accelerate the absorption of a biologically active agent into the systemic circulation. Typically the absorption-promoting agent will be administered with a biologically active substance such as a drug. Absorption promoting effect includes, but is not limited to, the ability to enhance the absorption of the biologically active agent by increasing the transport of the biologically active agent across the nasal mucosal membrane and to accelerate this transport.

Typically the administration of the absorption-promoting agent of the invention will cause or result in an enhanced pharmacological response to the biologically active agent of interest. In this context, "promoting" is intended to mean that the absorption of a biologically active agent is quantitatively greater and/or qualitatively better in the presence of the absorption-promoting agent than in the absence of the absorption-promoting agent. Furthermore, the absorption dynamics of the biologically active agent can be controlled through the concentration of the absorption enhancer, to tailor the pharmacokinetics to achieve the optimal biologically active response.

Comparisons of absorption in the presence and absence of the absorption-promoting agent can be performed by routine methods, such as titres comparisons by HPLC, LC-MS, LC-MS-MS, GC, GC-MS, spectroscopy or ELISA assays, and appropriate controls. The enhanced absorption can be a result of a direct effect on the mucosal membrane or due to a more advantageous presentation of the biologically active agent to the mucus membrane.

The method of the present invention comprises administering to a mammal, particularly a human or other primate, a pharmacologically effective dose of a biologically active agent composition comprising a biologically active agent and an absorption promoting agent amount according to the invention. The concentration of the absorption promoter ranges from high concentrations to low concentrations of from about 0.01% to about 2% v/v, and more particularly from about 0.2% to about 1.5% v/v and more preferably between about 0.2% and about 1% v/v, will typically be effective to provide an absorption promoting effects; however, variations in these dosage ranges will occur depending upon the biologically active agent. Moreover, the particular dosage will depend upon the age, weight and medical condition of the mammal to be treated, as well as on the method of administration. The skilled artisan will readily determine suitable doses.

The biologically active substance composition can be optionally administered in a pharmaceutically or physiologically acceptable vehicle, such as physiological or phosphate buffered saline, water, dextrose, ethanol polyols (such as glycerol or propylene glycol), and combinations thereof. The formulation according to the invention can be in admixture with a dispersing or wetting agent, suspending agent, and/or one or more preservatives. Suitable dispersing or wetting agents are, for example, naturally occurring phosphatides, e.g., lecithin, or soybean lecithin; condensation products of ethylene oxide with e.g., a fatty acid, a long chain aliphatic alcohol, or a partial ester derived from fatty acids and a hexitol or a hexitol anhydride, for example polyoxyethylene stearate, polyoxyethylene sorbitol monooleate, polyoxyethylene sorbitan monooleate etc. Suitable suspending agents are, e.g., naturally occurring gums such as, e.g., gum acacia, xanthan gum, or gum tragacanth; celluloses such as, e.g., sodium carboxymethylcellulose, microcrystalline cellulose (e.g., Avicel RC 591), methylcellulose; alginates such as, e.g., sodium alginate, etc. Suitable examples of preservatives for use in formulations according to the invention are parabens, such as methyl or propyl p-hydroxybenzoate, and benzalkonium chloride.

For application to the nasal mucosa nasal sprays or inhalation formulations are suitable compositions for use according to the invention. In a typical nasal formulation, the biologically active substance is present in the form of a solution. The pharmaceutically acceptable vehicles and excipients and optional other pharmaceutically acceptable materials present in the composition such as diluents, flavouring agents, preservatives and the like are all selected in accordance with conventional pharmaceutical practice in a manner understood by the persons skilled in the art. After administration of a nasal formulation according to the invention, the biologically active substance may be absorbed through the nasal mucosa.

Pharmaceutically acceptable excipients may include, antioxidants, buffering agents, preservatives, humectants and perfumes. Examples of antioxidants are ascorbic acid and derivatives thereof, tocopherol and derivatives thereof, butylated hydroxy anisole (BHA), and cysteine. Examples of preservatives are parabens, such as methyl or propyl p-hydroxybenzoate, and benzalkonium chloride. Examples of humectants are glycerin, propylene glycol, sorbitol, and urea. Examples of other excipients are edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sunflower oil, and teaseed oil; and of polymers such as carmelose, sodium carmelose, hydroxypropylmethylcellulose, hydroxyethylcellylose, hydroxypropylcellulose, chitosane, pectin, xanthan gum, carrageenan, locust bean gum, acacia gum, gelatin, and alginates.

Many mucosal formulations need some specialized mixture of excipients. Therefore formulations may comprise one or more surfactants and/or water absorbing polymers and/or substances which inhibit enzymatic degradation and/or alcohols, organic solvents, oils, pH-controlling agents, solubilizers, stabilizers, HLB-controlling agents, viscosity controlling agents, preservatives, osmotic pressure controlling agents, propellants, air displacement, water and mixture thereof. The surfactants may be selected from nonoxynol, octoxynol, tweens, spans, sodium lauryl sulfate, sorbitan monopalmitate; water absorbing polymers may be selected from glycofurols and derivatives thereof; polyethyleneglycol 200–7500 and derivatives thereof, polyvinylpyrrolidone, polyacrylic acid, propyleneglycol, gelatine, cellulose and derivatives thereof, substances which inhibit enzymatic degradation may be selected from aprotinin, DFP, carbopol; oils may be selected from vegetable oil, soybean oil, peanut oil, coconut oil, maize oil, olive oil, sunflower oil, Miglyols; pH-controlling agents may be selected from acetic acid, hydrochloric acid, nitric acid, potassium metaphosphate, potassium phosphate, sodium acetate, ammonia, sodium carbonate, sodium hydroxide, sodium borate, trolamine; solubilizers may be selected from alcohol, isopropyl alcohol, water, glycofurol, polyethyleneglycol 200–7500; stabilizers such as cyclodextrines; HLB controlling agents may be selected from Tween 20–85, Span 20–80, Brij 30–98, acacia; viscosity controlling agents may be selected from cellulose and derivatives thereof, Tweens and derivatives thereof, polyethyleneglycol and derivatives thereof, cetyl alcohol, glycerine, propylene glycol, sorbitol, gelatin; preservatives may be selected from benzalkonium salt, benzyl alcohol, phenol, thimerosal, phenylmercuric nitrate, phenylethyl alcohol, chlorobutanol, cetylpyridinium chloride; osmotic pressure controlling agents may be selected from dextrose, sodium chloride, mannitol; and propellants may be selected from dichlorodifluoromethane, dichlorotetrafluoroethane, trichloromonofluoromethane and other non-ozone damaging propellants such as butane; air displacement may be nitrogen.

It is essential that the effective amount of the biologically active substance can be administered in an appropriate volume. The volume should not exceed about 300 µl for a human subject when the composition is administered by the nasal route. A larger volume can be disagreeable to the patient and will drain out anteriorly through the nostrils or posteriorly toward the pharynx. The result is that a part of the biologically active substance is lost from the absorption site. The volume is preferably from about 20 µl to about 125 µl and preferably administered into one nostril.

Adjustment and manipulation of established dosage ranges used with desired pharmacological responses, is within the ability of those skilled in the art. The biologically active substances of the present invention are intended for use in the treatment of both immature and adult warm-blooded animals, and, in particular, humans, but also for diagnostic or prophylactic use.

The mucosal absorption-promoting agent, according to the invention, has a number of important implications. The agent can be used to tailor the absorption of a biologically active agent or drug to achieve optimal concentration over time, and hence desired physiological response. More specific, variations in the concentrations of the absorption promoter even in a low concentration range of from about 0.01% to about 2% can be used to manipulate the blood concentration of the drug over time. As a result, effective therapy, diagnosis or prophylactic treatment may be achieved. Additionally, the use of absorption-promoting agent of the invention can promote the ability of poorly absorbable substances to be transported across the mucosal membrane. It may also provide for safer drug delivery as the concentration can be controlled to meet the requirement for therapeutically concentration but may still be low enough to minimise the risk of toxic reaction. When the biologically active substance is toxic at the concentration normally required for effective therapy. By reducing the dose, the risk of toxic reaction is reduced. It may also provide for safer drug delivery.

Typically, an effective serum concentration of a biologically active substance is gained over a period of weeks or months. A clinically relevant concentration may be generated with much reduced time course by the mean of this invention. In some instances, it may result in the generation of a successful response in a single dose.

The formulation according to the invention is especially suitable for humans, including toddlers, adolescents, teenagers, adults and elderly. The nature of the formulation provides the ability to enhance and control the absorption of a variety of biologically active agents, and therefore the formulation may be used for subjects with various conditions such as humans with disease, e.g., splenectomized subjects, subjects with cancer, subjects using anticancer drugs, subjects using antiasthmatic drugs, subjects using anti-inflammatory drugs, subjects with hyper- and hypothyroidea, subjects having problems with malabsorption such as diarrhoea or emesis in addition to humans with nausea or those who have problems swallowing.

The formulation according to the invention is also suitable for administration to animals such as horses, sheep, dogs, cats, cows, pigs, goats, rabbits, wild animals and laboratory animals such as mice, rats, guinea pigs, hamsters, rabbits, dogs, cats or monkeys; to birds such as chickens, turkeys, ducks, ostrich, tropical birds or wild birds. For animals, the concentration of each component may need to be adjusted. For example for sheep, the nasal cavity has extremely high humidity, which may require addition of water absorbing excipients to the formulation. A person skilled in the art will know how to adjust the composition and the dosage amount in order to achieve a desired effect.

In a specific embodiment, the invention relates to a composition, comprising:

i) from about 0.01% to about 2.5% v/v of a PEG-(C8–C10) fatty acid mono- or diglyceride such as, e.g., glycerides sold under the trademarks Labrasol™ or Softigen™, ii) a triptan such as, e.g., sumatriptan, iii) optionally, a physiologically acceptable vehicle; and iv) water.

Further interesting embodiments appear from the appended claims.

The following Examples are included to illustrate the present invention and are not to be construed to limit the scope of this invention. The contents of all references, patents and published patent applications cited throughout this application are hereby incorporated by reference.

EXAMPLES

Example 1

Preparation of Compositions According to the Invention and In Vivo Behaviour in Rabbits Two formulations, A and B, were made. Formulation A contains Sumatriptan, 1% Softigen™ 767 (PEG-C8/C10-glyceride) in water; and Formulation B contains Sumatriptan in phosphate buffered saline, as Imigran®. These formulations were administered intranasally to rabbits and the sumatriptan serum concentration was determined as a function of time. The results show a significant improvement of $C_{max}$, $t_{max}$, bioavailability and clinical response when Softigen™ was used over the use of Imigran®. The FIGURE shows the results. $C_{max}$ was improved from 40 ng/ml to 600 ng/ml and $t_{max}$ was improved from 30–45 min and down to 3–5 minutes.

Example 2

Relationship Between the Concentration of Absorption Promoting Substance and the In Vivo Behaviour Four formulations, I, II and III, were made. Formulation I contains Sumatriptan, 1% Softigen™ 767 (PEG-C8/C10-glyceride) in water; Formulation II contains Sumatriptan, 0,5% Softigen™ 767 (PEG-C8/C10-glyceride) in water; Formulation III contains Sumatriptan, 0,2% Softigen™ 767 (PEG-C8/C10-glyceride) in water; and Formulation IV contains Sumatriptan in phosphate buffered saline, as Imigran®. These formulations were administered intranasally to rabbits and the sumatriptan serum concentration was determined as a function of time. The results show that the time to $t_{max}$ may be controlled with the use of right concentration of Softigen™ 767. Table 1 shows the results. There was a linear relationship between the concentration of Softigen™ 767 and time to $t_{max}$.

TABLE 1

| DRUG/Formulation | $t_{max}$ | |
|---|---|---|
| IMIGRAN ® | 31 min | (n = 8) |
| 0.2% SOFTIGEN ™ | 12.5 min | (n = 4) |
| 0.5% SOFTIGEN ™ | 8.5 min | (n = 3) |
| 1.0% SOFTIGEN ™ | 4.1 min | (n = 7) |

While this invention has been particularly shown and described with references to preferred embodiments thereof, it will be understood by those skilled in the art that various changes in form and details may be made therein without departing from the scope of the invention encompassed by the appended claims.

What is claimed is:

1. A pharmaceutical composition for nasal administration, comprising:
   i) a polyoxyethylene glycol (PEG)-fatty acid mono- or diglyceride having the formula (I):

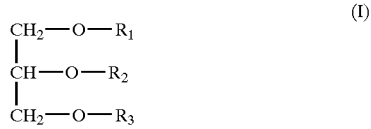

(I)

wherein R1, R2, and R3 are independently selected from the group consisting of $C_6$ to $C_{22}$ fatty acids, polyoxyethylene glycol (PEG) polymer and hydrogen, provided that it contains at least one $C_6$–$C_{22}$ fatty acid and at least one PEG polymer;
   ii) a triptan; and
   iii) optionally, a physiologically acceptable vehicle.

2. The composition according to claim 1, wherein the concentration of the PEG fatty acid mono-or diglyceride is from about 0.005% to about 2.5% v/v.

3. The composition according to claim 1, wherein the fatty acid is a $C_6$–$C_{18}$ fatty acid.

4. The composition according to claim 3, wherein the fatty acid is a $C_6$–$C_{14}$ fatty acid.

5. The composition according to claim 4, wherein the fatty acid is a $C_8$ or $C_{10}$ fatty acid or a combination thereof.

6. The composition according to claim 1, wherein the fatty acid is a saturated fatty acid.

7. The composition according to claim 1, wherein the PEG polymer has a molecular weight of from about 200 to about 1200.

8. The composition according to claim 1, wherein the PEG polymer is selected from the group consisting of:
   $PEG_{2-30}$ residues of polyoxyethylene having 2 to 30 polyoxyethylene units,
   $PEG_{2-20}$ residues of polyoxyethylene having 2 to 20 polyoxyethylene units,
   $PEG_{3-10}$ residues of polyoxyethylene having 3 to 10 polyoxyethylene units, and
   $PEG_{3-6}$ residues of polyoxyethylene having 3 to 6 polyoxyethylene units.

9. The composition according to claim 1, wherein the concentration of component i) is from about 0.005% to about 50% v/v.

10. The composition according to claim 9, wherein the concentration of component i) is from about 0.005% to about 40% v/v.

11. The composition according to claim 10, wherein the concentration of component i) is from about 0.01% to about 20% v/v.

12. The composition according to claim 11, wherein the concentration of component i) is from about 0.01 to about 10% v/v.

13. The composition according to claim 1, further comprising one or more components selected from the group consisting of surfactants, water absorbing polymers, substances which inhibit enzymatic degradation, alcohols, organic solvents, oils, pH-controlling agents, solubilizers, stabilizers, HLB-controlling agents, viscosity controlling agents, preservatives, osmotic pressure controlling agents, propellants, air displacement, water, and mixtures thereof.

14. The composition according to claim 1, wherein the triptan is sumatriptan.

15. A pharmaceutical composition for nasal administration, comprising:
   i) a polyoxyethylene glycol-fatty acid mono- or diglyceride having the formula (I):

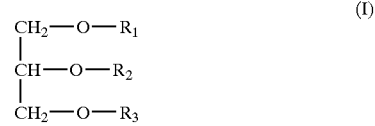

(I)

wherein $R_1$, $R_2$ and $R_3$ are independently selected from the group consisting of $C_8$ to $C_{10}$ fatty acids, polyoxyethylene glycol (PEG) polymer and hydrogen, provided that it contains at least one $C_8$–$C_{10}$ fatty acid and at least one PEG polymer, which is present in 0.01% to 2.5% v/v;
   ii) a triptan;
   iii) water, and present in 0.01% to 2.5% v/v;
   ii) triptan;
   iii) water, and
   iv) optionally a physiologically acceptable vehicle.

16. The composition according to claim 15, wherein the triptan is sumatriptan.

17. The composition according to claim 1, wherein the active substance enters systemic circulation.

18. A method of eliciting a pharmacological effect in a mammal including humans comprising administering to the mammal an effective amount of a pharmaceutical composition according to claim 1.

19. The method according to claim 18, wherein further comprising one or more components selected from the group consisting of surfactants, water absorbing polymers, substances which inhibit enzymatic degradation, alcohols, organic solvents, oils, pH-controlling agents, solubilizers, stabilizers, HLB-controlling agents, viscosity controlling agents, preservatives, osmotic pressure controlling agents, propellants, air displacement, water, and mixtures thereof.

20. A method of eliciting a pharmacological effect in a mammal comprising administering to the mammal an effective amount of a pharmaceutical composition according to claim 15.

21. A method for obtaining a fast onset of a therapeutic, prophylactic or diagnostic effect or a combination thereof of an active substance in a mammal including a human, comprising administering to the mammal an effective amount of a composition according to claim 1, the onset being faster when compared with a similar composition containing saline instead of component i) and using $t_{max}$ and/or $C_{max}$ as measures for the onset.

22. A method for improving the bioavailability of an active substance in a mammal including a human, comprising administering to the mammal an effective amount of a composition according to claim 1, the bioavailability being improved when compared with a similar composition containing saline instead of component i) and using $AUC_{0\text{-}infinity}$ as a measure.

23. The method according to claim 18, wherein the pharmaceutical composition is administered nasally.

24. The method according to claim 18, wherein the pharmaceutical composition is administered to human and wherein the volume of the pharmaceutical composition to be administered to the human ranges from about 20 to about 300 µL.

25. The pharmaceutical composition of claim 1, wherein the pharmaceutical composition consists essentially of the PEG fatty acid mono- or diglyceride, the triptan, optionally the physiologically acceptable vehicle and optionally one or more components selected from the group consisting of water absorbing polymers, substances which inhibit enzymatic degradation, alcohols, organic solvents, stabilizers, viscosity controlling agents, preservatives, osmotic pressure controlling agents, propellants, air displacement, and mixtures thereof.

26. The pharmaceutical composition of claim 1, wherein the pharmaceutical composition is non-irritating to the nasal mucosal membrane.

27. The pharmaceutical composition of claim 15, wherein the pharmaceutical composition consists essentially of the PEG fatty acid mono- or diglyceride, the triptan, water, optionally the physiologically acceptable vehicle and optionally one or more components selected from the group consisting of water absorbing polymers, substances which inhibit enzymatic degradation, alcohols, organic solvents, stabilizers, viscosity controlling agents, preservatives, osmotic pressure controlling agents, propellants, air displacement, water, and mixtures thereof.

28. The pharmaceutical composition of claim 15, wherein the pharmaceutical composition is non-irritating to the nasal mucosal membrane.

29. A pharmaceutical composition for nasal administration, consisting essentially of:

i) a polyoxyethylene glycol (PEG)-fatty acid mono- or diglyceride having the formula (I):

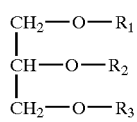

(I)

wherein R1, R2, and R3 are independently selected from the group consisting of $C_6$ to $C_{22}$ fatty acids, polyoxyethylene glycol (PEG) polymer and hydrogen, provided that it contains at least one $C_6$–$C_{22}$ fatty acid and at least one PEG polymer;

ii) sumatriptan;

iii) optionally, a physiologically acceptable vehicle; and iv) optionally one or more components selected from the group consisting of water absorbing polymers, substances which inhibit enzymatic degradation, alcohols, organic solvents, stabilizers, viscosity controlling agents, preservatives, osmotic pressure controlling agents, propellants, air displacement, and mixtures thereof.

30. A pharmaceutical composition for nasal administration, consisting essentially of:

i) a polyoxyethylene glycol (PEG)-fatty acid mono- or diglyceride having the formula (I):

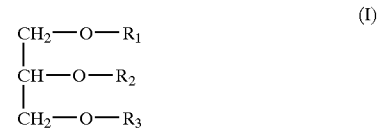

(I)

wherein R1, R2, and R3 are independently selected from the group consisting of a saturated $C_8$ fatty acid or a saturated $C_{10}$ fatty acid or a combination thereof, polyoxyethylene glycol (PEG) polymer and hydrogen, provided that it contains at least one saturated $C_8$ fatty acid or saturated $C_{10}$ fatty acid and at least one PEG polymer;

ii) a triptan;

iii) optionally, a physiologically acceptable vehicle; and iv) optionally one or more components selected from the group consisting of water absorbing polymers, substances which inhibit enzymatic degradation, alcohols, organic solvents, stabilizers, viscosity controlling agents, preservatives, osmotic pressure controlling agents, propellants, air displacement, and mixtures thereof.

31. The pharmaceutical composition of claim 30, wherein the triptan is sumatriptan.

32. The pharmaceutical composition of claim 31, wherein the PEG polymer is $PEG_{3\text{-}10}$ residues of polyoxyethylene having 3 to 10 polyoxyethylene units.

* * * * *

UNITED STATES PATENT AND TRADEMARK OFFICE
CERTIFICATE OF CORRECTION

PATENT NO.   : 6,855,332 B2
DATED        : February 15, 2005
INVENTOR(S)  : Sveinbjorn Gizurarson et al.

It is certified that error appears in the above-identified patent and that said Letters Patent is hereby corrected as shown below:

Column 12,
Line 34, delete "oxvethylene" and insert -- oxyethylene --.
Delete lines 39 and 40.
Line 67, after "a", add -- pharmaceutical --.

Signed and Sealed this

Seventh Day of June, 2005

JON W. DUDAS
*Director of the United States Patent and Trademark Office*